US00PP33489P2

(12) United States Plant Patent
Hansen

(10) Patent No.: US PP33,489 P2
(45) Date of Patent: Sep. 14, 2021

(54) **X *MANGAVE* PLANT NAMED 'WAVECREST'**

(50) Latin Name: **x *Mangave* times *Agave***
Varietal Denomination: Wavecrest

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,044

(22) Filed: Feb. 23, 2021

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/12
See application file for complete search history.

*Primary Examiner* — Keith O. Robinson

(57) ABSTRACT

A new and unique X *Mangave* plant named 'Wavecrest' characterized by a compact mound of lanceolate, variegated, coarsely sinuate, folded to concaved foliage. The foliage center is bluish-green and the marginal variegation is variable between yellowish and light chartreuse with a darker chartreuse intermediate zone. Marginal and apical spines are soft and flexible. Leaves develop small, irregular, greyed-purple spots with strong ultra violet light. The new plants is suitable for the garden landscape or as a potted plant in the garden or around the home.

1 Drawing Sheet

Botanical classification: hybrid; x *Mangave* times *Agave*.
Variety denomination: 'Wavecrest'.

BACKGROUND OF THE INVENTION

The present invention relates to the new and distinct X *Mangave* hybrid plant, x *Mangave* 'Wavecrest' discovered on Apr. 15, 2020 by the inventor at a wholesale perennial nursery in Zeeland, Mich., USA as a viviparous plantlet on a flower stem of a randomly variegated mutation of 'Catch a Wave', the original 'Catch a Wave' is assigned the U.S. Plant Pat. No. 29,723. Through trials at the same nursery the plant was originally assigned the breeder code 20-SP-MANG-959. The new plant has been successfully asexually propagated initially by scape offshoots at the same nursery in Zeeland, Mich. Viviparous plantlets have been found to produce stable and identical plants that maintain all the unique characteristics of the original plant.

No plants of x *Mangave* 'Wavecrest' have been sold, under this or any name, in this country or anywhere in the world, prior to the filing of this application, nor has any disclosure of the new plant been made prior to the filing of this application.

BRIEF SUMMARY OF THE INVENTION

X *Mangave* 'Wavecrest' differs from its parent as well as all other *Manfreda, Agave* and x *Mangave* known to the applicant. Compared with the parent the foliage of the new plant has stable variegation with the lighter coloration just on the margin. 'Catch a Wave' has similar coarse waves to the foliage, but the coloration is silvery blue-green with greyed purple spots.

The most similar cultivars known to the inventor are x *Mangave* 'Foxy Lady' U.S. Plant patent application Ser. No. 16/602,783 and 'Bridal Falls' U.S. Plant patent application Ser. No. 16/974,102. 'Foxy Lady' has a smaller size but has lighter creamy variegated leaf margins, the habit is more upright and the foliage is more glaucous and flatter with less undulation, with larger and sharper teeth, and the leaves are more numerous and do not have as obvious greyed-purple spotting. 'Bridal Falls' has a habit with more cascading foliage and the leaves are larger, less sinuate, the variegated margin is more creamy-white and the teeth are much larger.

The new plant, 'Wavecrest', is unique from each of the above cultivars and all *Agave*, X *Mangave* and *Manfreda* known to the inventor by the following combined traits:

1. Compact mound of lanceolate, coarsely sinuate foliage, folded to concaved;
2. The center of the foliage is bluish-green and the margin of the leaves is yellowish to light chartreuse with a darker chartreuse intermediate zone;
3. With intense ultraviolet light the foliage develops heavy, irregular, greyed-purple spots;
4. Teeth on leaves are soft and very flexible;
5. Moderate to rapid growth rate.

BRIEF DESCRIPTION OF THE DRAWING

The drawing of x *Mangave* 'Catch a Wave' demonstrates the overall appearance of a one-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
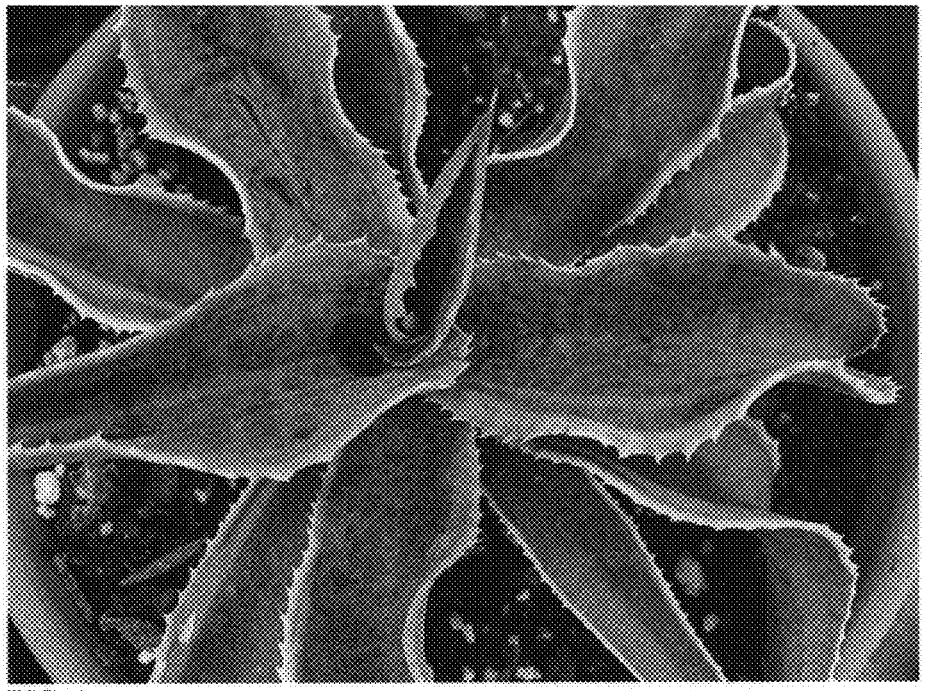
FIG. 1 shows a top view of the foliage of the new plant.
Figure 2:
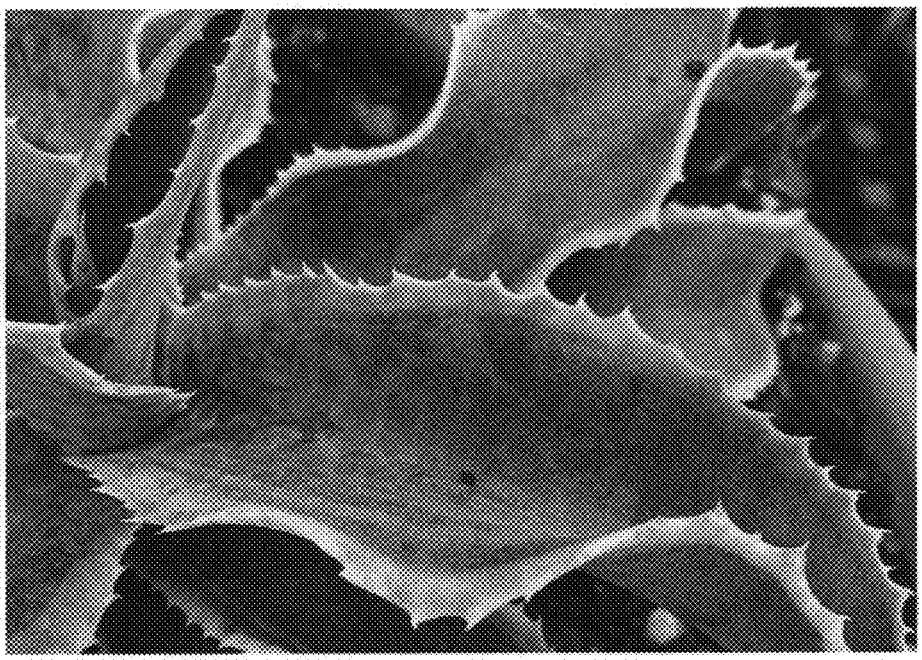
FIG. 2 shows a top side of the new plant.

The following descriptions and color references are based on the 2015 edition of The Royal Horticultural Society Colour Chart except where common dictionary terms are used. The new plant, x *Mangave* 'Wavecrest', has not been observed under all possible environments. The phenotype may vary slightly with different environmental conditions, such as temperature, light, fertility, moisture and maturity levels, but without any change in the genotype. The following observations and size descriptions are of a one-year-old plant in a commercial wholesale greenhouse in Zeeland, Mich. with supplemental water and fertilizer as needed.

Parentage: A randomly variegated mutation of 'Catch a Wave';

Propagation: Division of side shoots and sterile shoot-tip tissue culture;

Time to initiate roots from viviparous plantlet: About 21 days;

Growth rate: Moderate to rapid;

Crop time: About 12 to 14 weeks to finish in a 3.8 liter container from a 35 mm tissue culture growing at about 21° C.;

Rooting habit: Fleshy, lightly branching, with roots up to 15 cm long;

Root color: Variable depending on grow activity, and soil; between nearest RHS NN155C and RHS 161C;

Plant shape and habit: Succulent, frost-tender, herbaceous perennial with basal rosettes of about 15 leaves radially emerging outwardly from central stem, producing a radially-symmetrical, rounded mound;

Plant size: Foliage height about 50.0 cm tall from soil line to the top of the leaves and about 21.0 cm wide at the widest point slightly below soil line in container;

Foliage description: Lanceolate; simple; margins dentate with flexible teeth; slightly glaucous abaxial and adaxial; semi-lustrous adaxial and abaxial; glabrous abaxial and adaxial; teeth about 2.0 mm long, 3.0 mm wide at the base and spaced an average of about 5.0 mm apart; apex acute with sharp, flexible, apical spine; truncate sessile base; partially conduplicate; coarsely sinuate; with greyed-purple spots about 1.0 mm to 4.0 mm in diameter;

Leaf size: To about 16.0 cm long, about 4.5 cm wide naturally approximately one-thirds from base, about 0.4 cm thick at base and about 2.0 cm deep; adaxial margin width to about 11.0 mm wide near middle, abaxial margin to about 5.0 mm; adaxial intermediate portion nearest 7.0 mm wide, abaxial intermediate portion inconsistent, to about 2.0 mm wide when present; adaxial center portion to about 33.0 mm wide and abaxial center portion to about 50.0 mm wide;

Foliage fragrance: None observed;

Leaf blade color:

*Adaxial*.—Margin between RHS 151D and RHS 8B in distal portion and between RHS N144D and RHS 145A in the proximal portion with spots nearest RHS 137C in both distal and proximal portion and intensifying with ultraviolet light exposure to nearest RHS N186C; center between RHS NN137A and RHS 139A with spots nearest RHS 136A intensifying to between RHS N186C and RHS N186B in high ultraviolet light; intermediate portion nearest RHS 146B with spots an overlay nearest RHS N186C.

*Abaxial*.—Margin distal portion between 151D and RHS 8B and proximal potion between RHS N144D and RHS 145A with spots between RHS 145A and RHS 146D intensifying with ultraviolet exposure to an overlay of nearest RHS N186C; center nearest RHS 137B with spots of nearest RHS 137A and intensifying to an overlay of nearest RHS N186C; intermediate layer nearest RHS 146C with spots nearest RHS 144A.

*Teeth*.—Variable nearest RHS 145C and between RHS 151D and RHS 8B.

Apical spine: Small, sharp and flexible; about 2.0 to 3.0 mm long and less than 1.0 mm across at base;

Apical spine color: Between RHS 166A and RHS 166B;

Petiole: Leaves sessile;

Veins: Parallel; not distinct abaxial or adaxial;

Inflorescence description: Not yet observed;

Fruit and seed not observed;

Disease resistance: X *Mangave* 'Wavecrest' has not been observed to be resistant to diseases beyond that which is normal for X *Mangave, Agave* or *Manfreda*. The new plant is xeromorphic and survives well with minimal water once established. The new plant is hardy to least USDA zone 10. Full extent of winter hardiness has not been tested.

It is claimed:

1. A new and distinct cultivar of ornamental X *Mangave* plant named 'Wavecrest' as herein described and illustrated.

* * * * *